United States Patent
Zhu et al.

(10) Patent No.: US 11,385,171 B2
(45) Date of Patent: Jul. 12, 2022

(54) METHODS FOR DETECTING AND QUANTIFYING TETRAKIS (HYDROXYMETHYL)PHOSPHONIUM SULFATE (THPS) IN BIOCIDE PRODUCTS

(71) Applicant: Saudi Arabian Oil Company, Dhahran (SA)

(72) Inventors: Xiangyang Zhu, Dhahran (SA); Mohammed A. Moniee, Dhahran (SA); Mazen A. Al-Saleh, Khobar (SA)

(73) Assignee: Saudi Arabian Oil Company, Dhahran (SA)

( * ) Notice: Subject to any disclaimer, the term of this patent is extended or adjusted under 35 U.S.C. 154(b) by 119 days.

(21) Appl. No.: 17/084,108

(22) Filed: Oct. 29, 2020

(65) Prior Publication Data

US 2022/0136965 A1    May 5, 2022

(51) Int. Cl.
*G01N 21/33* (2006.01)
*A01N 57/34* (2006.01)
*G01N 21/78* (2006.01)

(52) U.S. Cl.
CPC ............. *G01N 21/33* (2013.01); *A01N 57/34* (2013.01); *G01N 21/78* (2013.01)

(58) Field of Classification Search
CPC ......... G01N 21/33; G01N 21/78; A01N 57/34
See application file for complete search history.

(56) References Cited

U.S. PATENT DOCUMENTS

| | | |
|---|---|---|
| 9,772,287 B2 | 9/2017 | Al-Moniee et al. |
| 2014/0253721 A1 | 9/2014 | Walicki |
| 2015/0185208 A1 | 7/2015 | Pinkowitz |
| 2017/0044035 A1 | 2/2017 | Underwood et al. |
| 2017/0102370 A1 | 4/2017 | Alber et al. |
| 2018/0340113 A1 | 11/2018 | Chen et al. |

FOREIGN PATENT DOCUMENTS

| | | |
|---|---|---|
| EP | 0016578 A1 | 10/1980 |
| WO | 2018037242 A1 | 3/2018 |
| WO | 2019025819 A1 | 2/2019 |

OTHER PUBLICATIONS

Thaís Tamye Marques, et al., "Determination of tetrakis (hydroxymethyl) phosphonium sulfate in commercial formulations and cooling water by capillary electrophoresis with contactless conductivity detection." Journal of Separation Science 38.5 (2015): 852-857.

(Continued)

*Primary Examiner* — Jennifer Wecker
*Assistant Examiner* — Kathryn Elizabeth Limbaugh
(74) *Attorney, Agent, or Firm* — Leason Ellis LLP (57) ABSTRACT

The present application discloses methods for detecting and quantifying tetrakis(hydroxymethyl) phosphonium sulfate (THPS) in a water sample. In the methods, a water sample is mixed with a $KMnO_4$ solution to form a mixture. An intensity of $KMnO_4$ absorption in the mixture is then measured at a wavelength of 525 nm. The measured intensity is normalized by subtracting a background intensity at a wavelength of 650 nm. The presence and concentration of THPS in the water sample can then be determined by comparing the normalized intensity with intensity values of $KMnO_4$ absorption of calibration samples comprising $KMnO_4$ and known THPS concentrations.

20 Claims, 8 Drawing Sheets

(56) References Cited

OTHER PUBLICATIONS

Gros, Nataša. "A novel type of tricolour light-emitting-diode-based spectrometric detector for low-budget flow-injection analysis." Sensors 7.2 (2007): 166-184.
LaMotte Company, "Solvay Tolcide PS Biocides Test Kit: Determination of Tetrakishhydroxymethyl Phosphonium Sulfate (THPS) in Tolcide PS Biocides". Instruction Manual. 1-2.
Tintometer Inc. "Lovibond THPS Kit: Part No. 56K001601." Instruction Manual. pp. 1-4.
Chaneam, S., et al. "P1AP. 5-New Fluorescence Sensor for Online Monitoring of Copper (II) Ion in Food Supplements." Proceedings IMCS 2018 (2018): 444-445.
International Search Report and Written Opinion in a corresponding PCT Application No. PCT/US2021/072053 dated Feb. 4, 2022.
Zenki Michio et al: Repetitive Determinaton of Chamical Oxygen Demand by Cyclic Flow Injection Analysis Using On-line Regeneration of Consumed Permanganate; Analytical Sciences col. 22, No. 1. 206, pp. 77-80.

Fig. 6

METHODS FOR DETECTING AND QUANTIFYING TETRAKIS (HYDROXYMETHYL)PHOSPHONIUM SULFATE (THPS) IN BIOCIDE PRODUCTS

TECHNICAL FIELD

The present disclosure is generally related to detection and quantification of a compound in a biocide composition.

BACKGROUND OF THE DISCLOSURE

Tetrakis(hydroxymethyl)phosphonium sulfate (THPS) is the main active component in biocide products commonly used in the oil and gas industry for microbial control in water systems. The THPS-based biocides are generally considered environment-friendly since they are readily degradable.

THPS is traditionally detected and quantified using iodometric titration methods or various commercial test kits. For example, the Solvay TOLCIDE Biocides Test kit and LOVIBOND THPS kit are commonly used commercial test kits. However, these test kits have a limited detection range for THPS (e.g., 0-100 ppm).

Additionally, in a large water pipeline network or other large water systems, it is difficult with currently available methods and test kits to collect water samples for biocide residual measurements at downstream locations after a batch treatment of the biocide product is provided at an upstream location. This is due to the difficulties in estimating the biocide travel time in a large pipeline network because of the complexity of pipeline networks (e.g., diameters, branches, etc.) and daily operation changes and fluctuations (e.g., flow rate).

As such, there is a need for effective field measurement methods for biocides, and in particular, THPS-based biocides, in oil and gas facilities. The present application addresses these and other challenges related to measuring THPS in water, and specifically in water networks of oil and gas facilities.

SUMMARY OF THE DISCLOSURE

In a first aspect, a method for detecting tetrakis(hydroxymethyl)phosphonium sulfate (THPS) in a water sample, is provided. In the method, a water sample is mixed with a $KMnO_4$ solution to form a mixture. An intensity of $KMnO_4$ absorption in the mixture is measured at a wavelength of 525 nm. The measured intensity is then normalized by subtracting a background intensity at a wavelength of 650 nm. A presence of THPS in the water sample is then determined by comparing the normalized intensity with intensity values of $KMnO_4$ absorption of calibration samples comprising $KMnO_4$ and known THPS concentrations.

In another aspect, the water sample is mixed with the $KMnO_4$ solution for approximately 2 minutes. In another aspect the water is fresh water or salt water. In a further aspect, the salt water is Arabian Gulf Seawater.

In another aspect, the mixture comprises equal volumes of the water sample and the $KMnO_4$ solution. In another aspect, the intensity of the $KMnO_4$ absorption in the mixture is measured using a sensor. In a further aspect, the sensor comprises a 565 nm LED and a 650 nm LED attached to a Z-flow cell. In a further aspect, the water sample is collected from water flowing in a conduit, and the sensor is an online sensor in fluid connection with water conduit and configured to perform real-time measurements of the water flowing in the conduit.

In another aspect, the limit of detection for THPS in the water sample is approximately 2 ppm.

In a second aspect, a method for quantifying tetrakis(hydroxymethyl)phosphonium sulfate (THPS) in a water flowing in a conduit is provided. In the method, a water sample comprising THPS from the conduit is mixed with a $KMnO_4$ solution, such that the THPS in the water sample reacts with the $KMnO_4$ solution. An intensity of the $KMnO_4$ absorption is measured in the mixture at a wavelength of 525 nm. The measured intensity is then normalized by subtracting a background intensity at a wavelength of 650 nm. A concentration of THPS in the water sample is determined based on a comparison between the normalized intensity and intensity values of $KMnO_4$ absorption of calibration samples comprising $KMnO_4$ and known THPS concentrations.

In another aspect, the determined concentration of THPS is accurate for water samples having a THPS content of approximately 2-500 ppm. In another aspect, the water sample comprises a THPS-based biocide. In another aspect, the water sample is mixed with the $KMnO_4$ solution for at least 2 minutes.

In another aspect, the water is fresh water or salt water. In a further aspect, the salt water is Arabian Gulf Seawater (AGS). In a further aspect, the dynamic range of concentration of THPS in AGS is approximately 5-1500 ppm.

In another aspect, the mixture comprises equal volumes of the water sample and the $KMnO_4$ solution. In another aspect, the intensity of the $KMnO_4$ absorption in the mixture is measured using a sensor. In a further aspect, the sensor comprises a 565 nm LED and a 650 nm LED attached to a Z-flow cell. In a further aspect, the sensor is an online sensor in fluid connection with the conduit and configured to perform real-time measurements.

DETAILED DESCRIPTION OF CERTAIN EMBODIMENTS

By way of overview and introduction, the present application discloses methods for detecting and quantifying tetrakis(hydroxymethyl)phosphonium sulfate (THPS) in a water sample. In one or more embodiments of the method, a water sample comprising THPS (or suspected of comprising THPS) is mixed with a $KMnO_4$ solution to form a mixture. An intensity of $KMnO_4$ absorption in the mixture at a wavelength of 525 nm is then measured. Once the intensity of $KMnO_4$ absorption at 525 nm in the mixture has been measured, the measured intensity of $KMnO_4$ absorption is normalized by subtracting a background intensity at a wavelength of 650 nm. The normalized intensity of $KMnO_4$ absorption measurement is then used to determine the presence and/or concentration of THPS in the water sample by comparing the normalized intensity of KMnO4 absorption with $KMnO_4$ absorption intensity values of calibration samples comprising $KMnO_4$ and known THPS concentrations.

These and other aspects of the present methods are described in further detail below with reference to the accompany drawing figures, in which one or more illustrated embodiments and/or arrangements of the methods are shown. The methods of the present application are not limited in any way to the illustrated embodiments and/or arrangements. It should be understood that the methods as shown in the accompanying figures are merely exemplary of the methods of the present application, which can be embodied in various forms as appreciated by one skilled in the art. Therefore, it is to be understood that any structural and functional details disclosed herein are not to be interpreted as limiting the present methods, but rather are provided as a representative embodiment and/or arrangement for teaching one skilled in the art one or more ways to implement the present methods.

Further, it should be understood that, as used in the present application, the term "approximately" when used in conjunction with a number refers to any number within 5% of the referenced number, including the referenced number.

Figure 1:
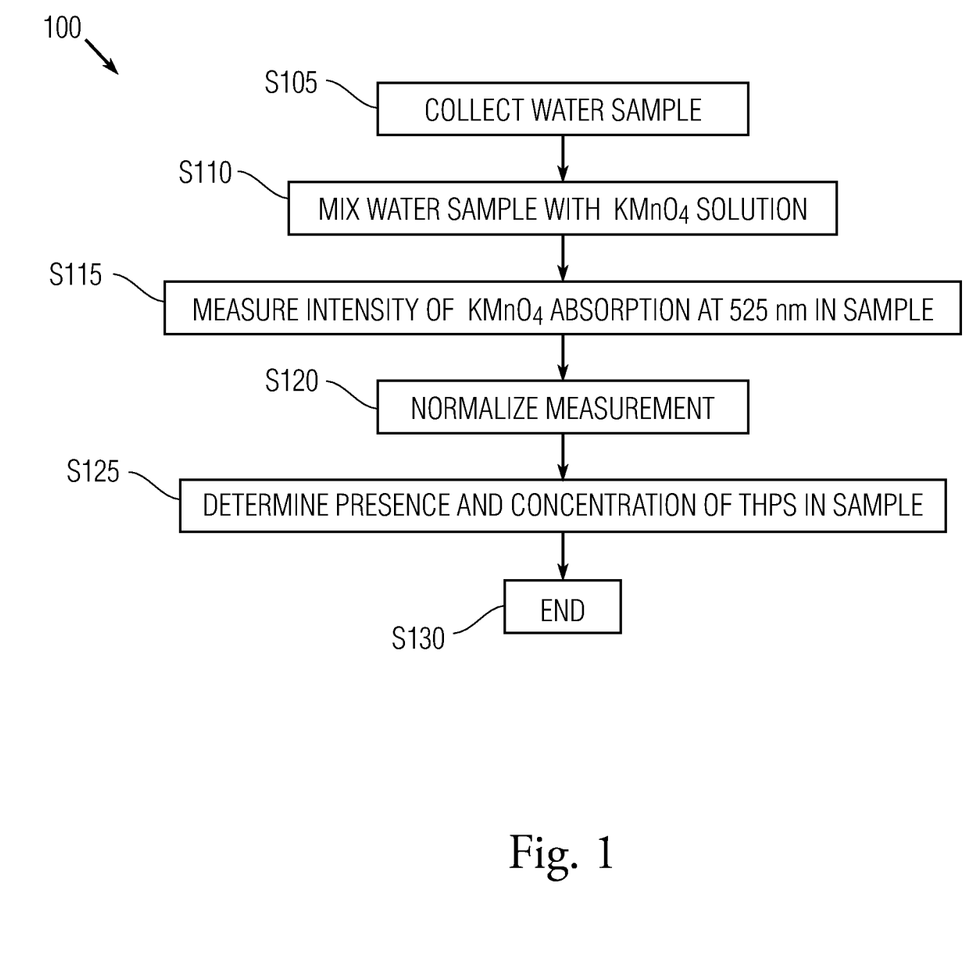
FIG. 1 displays a flow diagram of steps for a method for detecting and quantifying THPS in a water sample in accordance with one or more embodiments.

Referring now to FIG. 1, a flow diagram displaying steps for a method 100 for detecting and quantifying THPS in a water sample is provided in accordance with one or more embodiments. The method 100 begins at step S105 where a water sample is collected. The water sample comprises or is suspected of comprising THPS or a THPS-containing biocide. The water sample can be a freshwater sample or a saltwater sample, such as Arabian Gulf Seawater (AGS). AGS has a salinity around 57,000 mg/L, which is much higher than the average salinity in the world's oceans (approximately 35,000 mg/L).

In one or more embodiments, the water sample can be collected from an existing body of water, or from a water treatment facility or water distribution network known to comprise THPS or THPS-based biocides. Thus, in embodiments in which the water is collected from a water treatment facility, for example, the water can be collected from a conduit of the water treatment facility.

At step S110, the collected water sample is mixed with a potassium permanganate ($KMnO_4$) solution to form a mixture. In one or more embodiments, equal amounts of the water sample and the $KMnO_4$ solution are mixed together. In one or more embodiments, the $KMnO_4$ solution is a 0.5 to 2.5 millimolar (mM) $KMnO_4$ solution. In at least one embodiment, the $KMnO_4$ solution is a 1-2 millimolar (mM) $KMnO_4$ solution. The $KMnO_4$ solution can have a pH of approximately 5.0 in accordance with one or more embodiments. In at least one embodiment, the $KMnO_4$ solution comprises water that has been deionized to a high degree and purified using resin filters, such as a water purified using the MILLI-Q® Water Purification System ("MILLI-Q water").

In at least one preferred embodiment, the $KMnO_4$ solution is a 1 mM $KMnO_4$ in MILLI-Q water (pH 5.0).

The collected water sample and the $KMnO_4$ solution are mixed for a period sufficient to enable a reaction between the $KMnO_4$ solution and the THPS in the water sample. In accordance with one or more embodiments, in the reaction, the inventors determined that the mole ratio of the reaction between THPS and permanganate is approximately 2:1, meaning that 2 moles of THPS is able to decolorize 1 mole of $KMnO_4$. In at least one embodiment, the water sample is mixed with the $KMnO_4$ solution for at least 2 minutes. In one or more embodiments, the water sample is mixed with the $KMnO_4$ solution for approximately 1 to 5 minutes. In one or more preferred embodiments, the water sample is mixed with the $KMnO_4$ solution for approximately 2 minutes.

At step S115, the $KMnO_4$ absorption in the water-$KMnO_4$ mixture is measured at a wavelength of 525 nm. As mentioned above, when the water sample and $KMnO_4$ solution are mixed, THPS present in the water sample reacts with the $KMnO_4$ solution. Thus, as determined by the inventors, when THPS is present in the water sample, the resulting measured absorption at 525 nm of the $KMnO_4$ solution following reaction with the THPS is correlated with THPS concentration in the water sample. Thus, by measuring the absorption change of the $KMnO_4$ solution after the reaction with THPS, the THPS concentration in the water sample (or the THPS concentration in the biocide product in the water sample) can be determined.

In one or more embodiments of the present methods, the THPS concentration in the water sample can be accurately determined for water samples comprising THPS in a range of approximately 5-1500 ppm. In other words, in one or more embodiments, the present methods have a dynamic range of approximately 5-1500 ppm for THPS. This dynamic range applies to freshwater samples and saltwater samples. This concentration range covers the normal biocide treatment concentration and residual concentration encountered in water treatment facilities and distribution networks in the oil and gas industry.

At step S120, the measured absorption of $KMnO_4$ at the wavelength of 525 nm is normalized by subtracting the background intensity at the wavelength of 650 nm. More specifically, the measured absorption of $KMnO_4$ at the wavelength of 525 nm represents the $KMnO_4$ color change after the reaction with THPS. At step S120, the absorption of $KMnO_4$ in the mixture at the wavelength of 650 nm is measured, which corresponds to the background absorption (background intensity) of the solution. The measured absorption of $KMnO_4$ at the wavelength of 525 nm is then normalized by subtracting the measured absorption of $KMnO_4$ at 650 nm (the background intensity). Normalization by subtracting the 650 nm background absorption improves the lower detection limit of THPS in the present methods.

At S125 the presence and concentration of THPS in the water sample is determined. The presence and concentration of THPS in the water sample is determined by comparing the normalized absorption measurement of $KMnO_4$ at the wavelength of 525 nm with intensity values of calibration samples comprising $KMnO_4$ and known THPS concentrations.

To begin step S125, a correlation equation (or calibration curve) is established between the THPS concentration in a given water sample and the measured normalized absorption (intensity) of $KMnO_4$. As determined by the inventors, a change in absorption (intensity) due to the reaction of the THPS and of $KMnO_4$ is correlated with the concentration of THPS in the water sample. As such, based on this correlation, a calibration curve is established between the THPS concentration in given samples and normalized absorption of the $KMnO_4$. As with the absorption measurements at step S120, the absorption of $KMnO_4$ in the samples for the calibration curve are normalized by subtracting the 650 nm background absorption. Using the established calibration curve, the concentration of THPS in the water sample is determined by matching the normalized measured absorption of the $KMnO_4$ at the wavelength of 525 nm with its normalized absorption (intensity) value on the curve and the corresponding THPS concentration value on the curve.

Figure 2A:
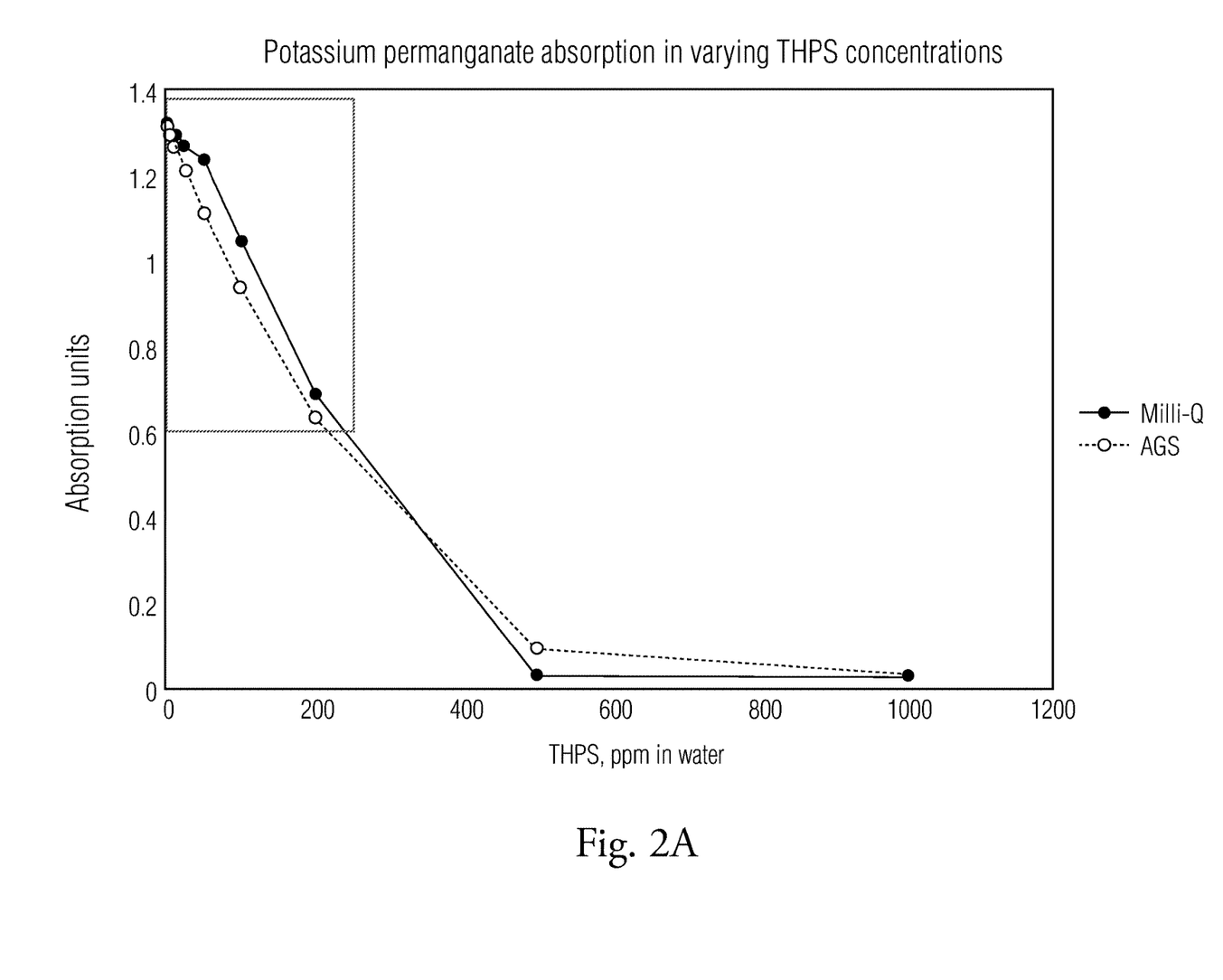
FIGS. 2A-2B display graphs showing the $KMnO_4$ absorption at 525 nm as a function of THPS concentration in samples of Arabian Gulf Seawater (AGS) and Milli-Q water in accordance with one or more embodiments.
Figure 2B:
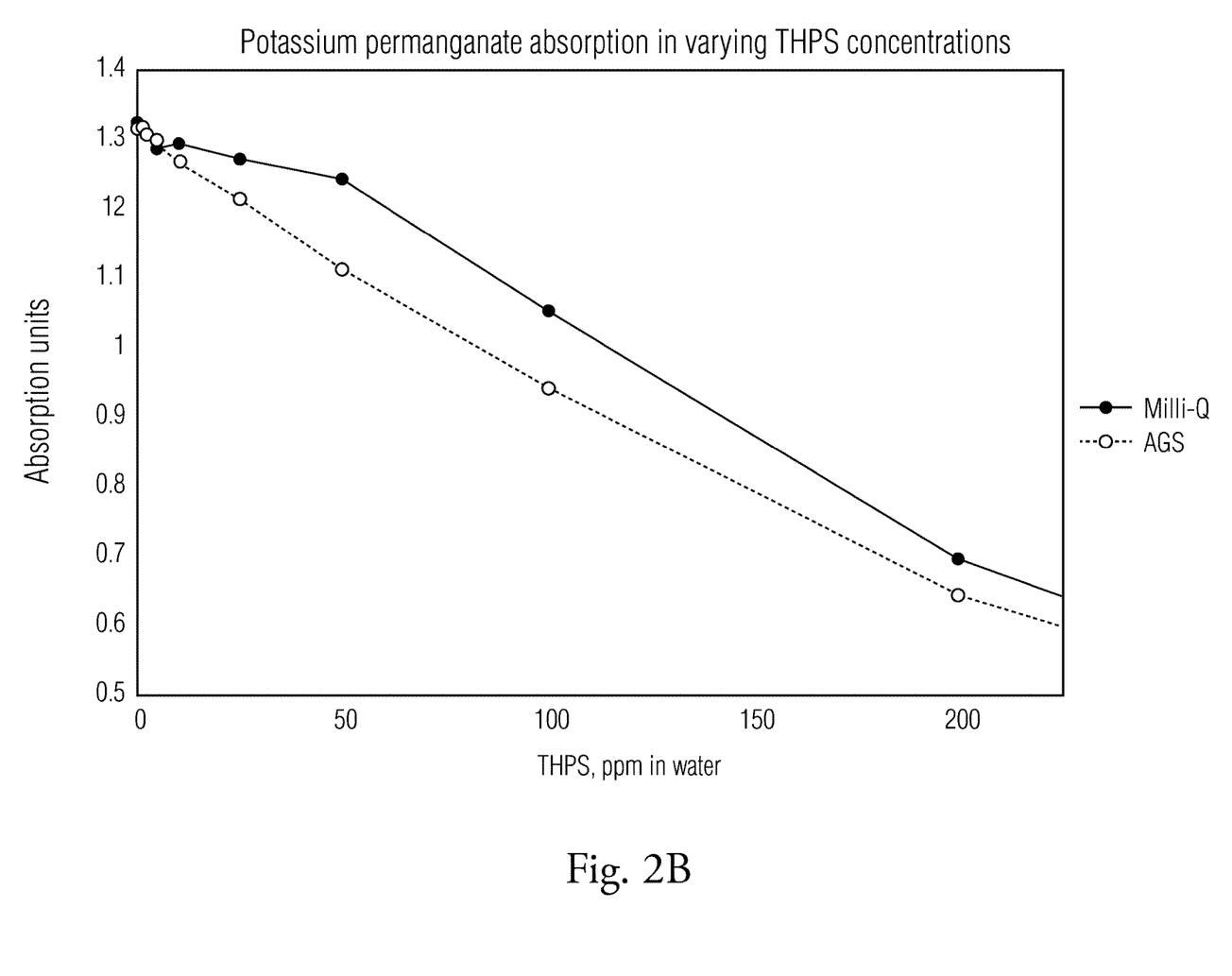

FIGS. 2A-2B show example graphs showing the absorption of $KMnO_4$ absorption at 525 nm as a function of THPS concentrations in samples of Arabian Gulf Seawater (AGS) and Milli-Q water in accordance with one or more embodiments. AGS is widely used in the Middle East region for reservoir injection for pressure maintenance of oil reservoirs. The AGS is transported through complex pipeline network for reservoir injection, and the microbial activities in the AGS are controlled by biocide treatment (e.g., THPS).

In the examples of FIGS. 2A-2B, samples comprising 0 to 1000 ppm of THPS were prepared in AGS and Milli-Q water. Equal volumes (1.5 mL) of the THPS-containing sample (both AGS and Milli-Q water) and 1.0 mM $KMnO_4$ (pH 5.0) were mixed and allowed to react for 2 minutes. Then, the intensity of the permanganate ($KMnO_4$) absorption at 525 nm was measured and normalized by subtracting the background intensity at 650 nm. FIG. 2A shows the $KMnO_4$ absorption at 525 nm as a function of THPS concentrations (0-1000 ppm), and FIG. 2B shows a zoomed in version of the 0-200 ppm region of the graph of FIG. 2A.

As shown in the graphs of FIGS. 2A-2B, a linear relationship between the concentrations of THPS and absorption of $KMnO_4$ is established. Specifically, in accordance with one or more embodiments, the absorption of $KMnO_4$ showed a linear relationship with THPS at the range of THPS concentrations between approximately 0 and 200 ppm, with a dynamic range of approximately 2-500 ppm. In one more embodiments, the dynamic range can be expanded to approximately 5-1500 ppm of THPS by increasing the concentration of the $KMnO_4$ solution. For example, at a concentration of 1 mM for $KMnO_4$ at 525 nm, the dynamic range is approximately 2-500 ppm. However, at a concentration of 2 mM for $KMnO_4$ at 525 nm, the dynamic range increases to approximately 5-1500 ppm. The results shown in FIGS. 2A-2B also indicate that the function of THPS concentration with 1 mM $KMnO_4$ absorption at 525 nm is comparable in Milli-Q water samples and AGS samples, and that THPS can be detected at levels as low as 2 ppm, and as high as 500 ppm, in accordance with one or more embodiments. In at least one embodiment, the dynamic range for detection of THPS in the water samples a ta concentration of 2 mM for $KMnO_4$ at 525 nm is approximately 10-700 ppm. The above dynamic ranges are applicable to freshwater and saltwater samples.

Thus, in one or more embodiments, the limit of detection is approximately 2 ppm. In one or more embodiments, the dynamic detection range for THPS concentration in the sample is approximately 2-500 ppm. Further, in at least one embodiment, by increasing KMnO4 concentration from 1 mM to 2 mM, the dynamic range of the THPS in AGS can be expanded to approximately 5-1500 ppm.

Figure 3A:
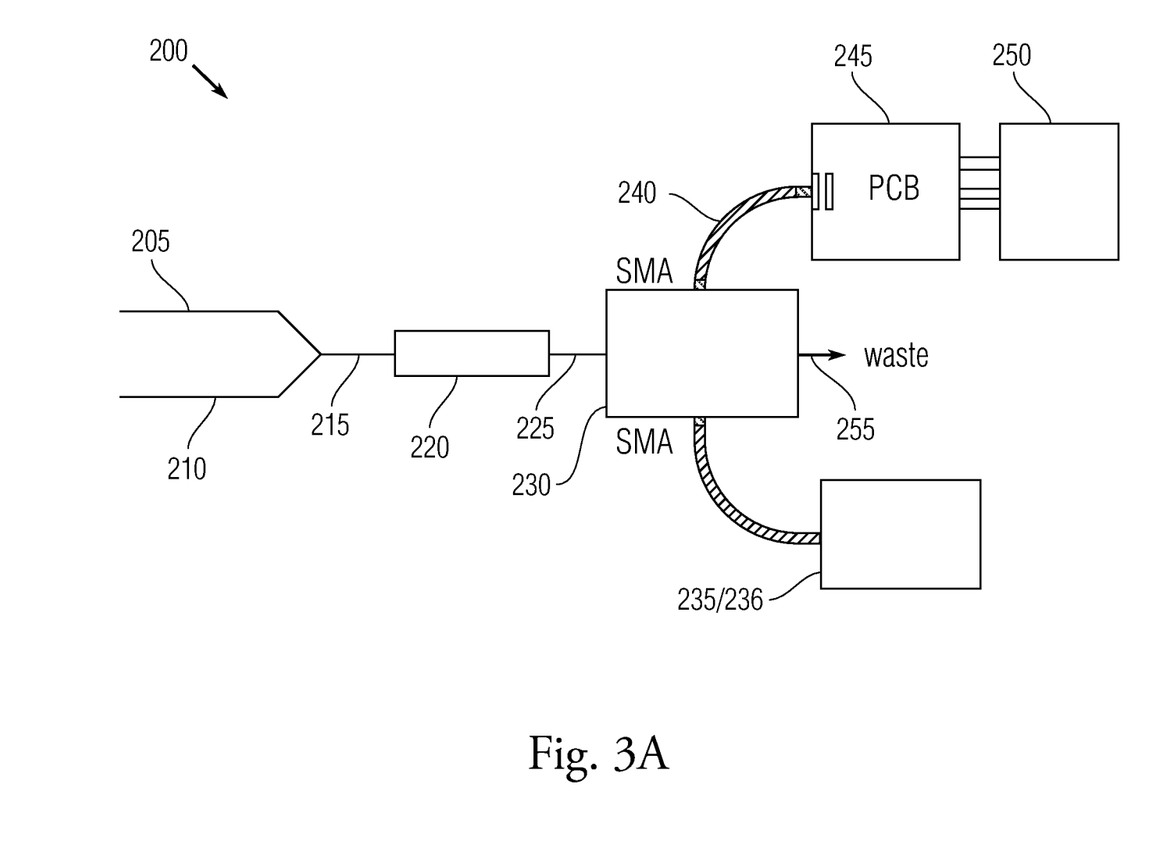
FIGS. 3A-3B show diagrams of various aspects of an exemplary THPS sensor for use in the present methods in accordance with one or more embodiments.
Figure 3B:
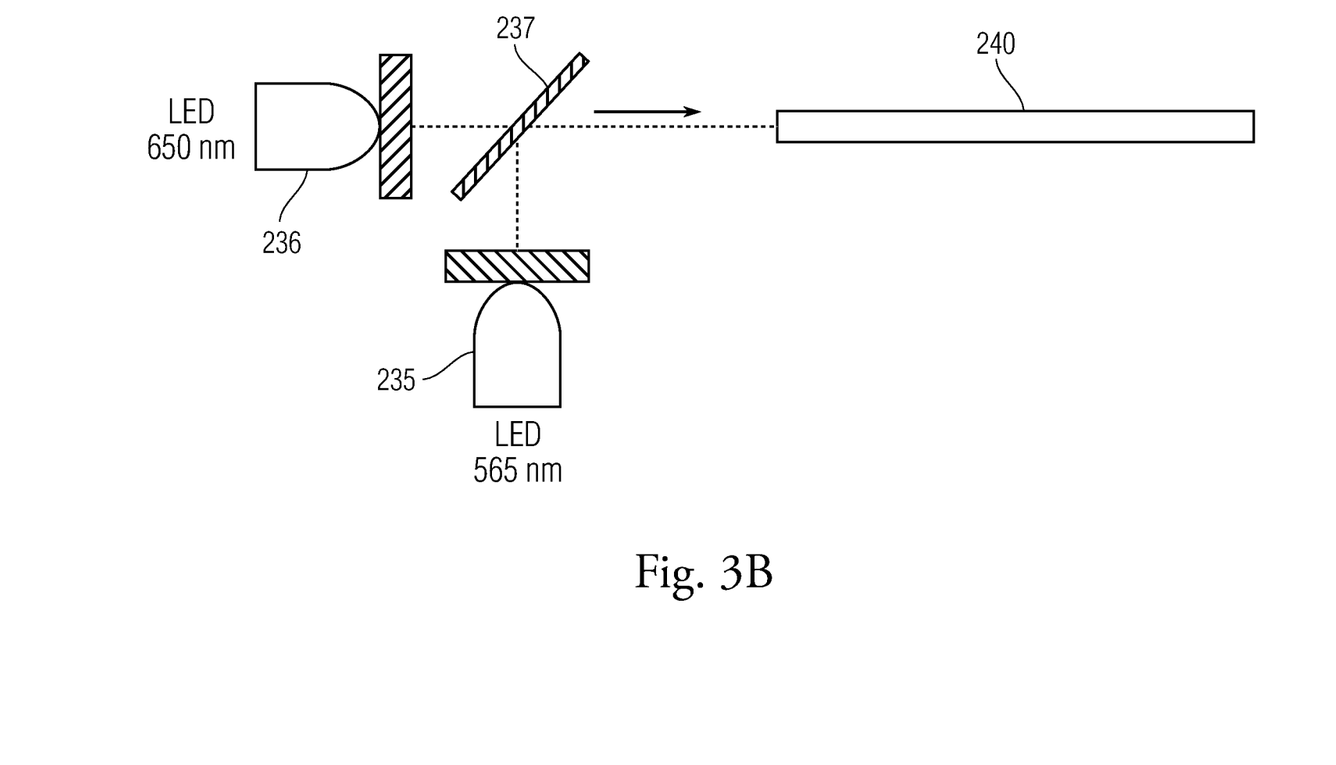

Returning to FIG. 1, after the concentration of THPS in the water sample is determined, the method ends at step S130. In at least one embodiment, the steps of the present method (steps S105-S130) are completed using a sensor. FIGS. 3A-3B display various aspects of an exemplary THPS sensor 200 for the present methods in accordance with one or more embodiments. With reference to FIG. 3A, the sensor 200 comprises a sample reservoir 205 for the water sample comprising THPS and a reservoir 210 for the $KMnO_4$ solution. The THPS sensor 200 also includes a first conduit 215 for transferring the water sample comprising THPS and the $KMnO_4$ solution from their respective reservoirs to a mixing coil 220. In the mixing coil 220, the water sample comprising THPS and the $KMnO_4$ solution are mixed (step S110). Following mixing, the mixture is transferred via a second conduit 225 to a flow cell 230. In one or more embodiments, the flow cell 230 is a Z-flow cell.

With continued reference to FIGS. 3A and 3B, in one or more embodiments the sensor 200 further includes a 565-nm light-emitting diode (LED) 235 and a reference 625-nm LED 236, which are operatively attached to the flow cell 230. In at least one alternative embodiment, the two LEDs 235 and 236 can be replaced with a multicolor LED. In the flow cell 230, the mixture comprising the water sample and the $KMnO_4$ solution is exposed to the light emitted by the two LEDs 235 and 236 for absorption measurement.

In accordance with one or more embodiments, FIG. 3B shows a preferred optical configuration for the Z-flow cell, in which the 565-nm light-emitting diode (LED) 235 and the reference 625-nm LED 236 are arranged perpendicularly and directed at a dichroic mirror 237. In such an embodiment, the THPS sensor 200 optimizes the light levels that are coupled into the flow cell by introducing a reference channel (650 nm LED). In one or more embodiments, the Z-flow cell is a typical Z-flow cell having a Z-shaped fluidic path, which allows continuous flow up through the flow cell, and minimizes bubble entrapment. When combined with spectrometers, light sources and accessories, a Z-flow cell allows rapid analysis of the samples by measuring the optical absorbance of fluids moving through the flow injection system. Different optical pathlengths and internal volumes in Z-cells are available depending on the analytical needs. As shown in FIG. 3A, the Z-flow cell 230 can include SMA connectors for attachment to optical configuration and the microcontroller, respectively. In a preferred optical configuration for the Z-flow cell shown FIG. 3B, the two LED lights 235, 236 with specific wavelengths (565 nm and 650 nm, respectively) pass through the fluid ($KMnO_4$ and sample mixture) and the absorption is measured by a spectrometer.

Referring again to FIG. 3A, in one or more embodiments, the flow cell 230 (e.g., Z-flow cell) has an absorption path length of approximately 1 cm. When the absorption of the $KMnO_4$ is collected by the flow cell 230, a signal is transported via a patch cable 240 (e.g., 1.5 mm patch cable with an SMA connector) to a microcontroller 245 (e.g., printed circuit board [PCB] microcontroller). A micro-processor platform 250 (e.g., Feather, Arduino technology) can process the analogue signals and provide pulses in order to measure the absorption of the $KMnO_4$ (e.g., step S115). After the absorption of the $KMnO_4$ has been measured and the concentration of THPS in the sample has been determined, the mixture of the THPS water sample and the $KMnO_4$ is passed out of the flow cell 230 via a third conduit 255 and can be disposed of as waste.

In one or more embodiments, the THPS sensor 200 is an online sensor that is operatively connected to a water treatment facility or water distribution network, for example, such that real-time measurements of THPS in the water treatment facility or water distribution network can be determined. In one or more embodiments, the sensor 200 can also be configured to transmit measurements (wired or wireless transmissions) and data to a control center remote from the sensor 200.

In at least one embodiment, the absorption measurements can be performed with instruments other than a sensor. For example, lab-based instruments can be used to measure the absorption of the $KMnO_4$ mixture. Such lab-based instruments can include, for example, spectrometers or spectrophotometers. Examples of suitable spectrophotometers are Mettler Toledo Spectrophotometer UV5 and UV7 and Konica Minolta Spectrophotometer CM-5 and CM-3600A.

The above aspects and other aspects of the present methods can be further understood through the following examples.

Example 1

A biocide product, approximated as containing 20-40% THPS and 10-20% surfactant, was used in this experiment. The biocide product was diluted in AGS into samples comprising approximately 0, 1, 2, 5, 10, 25, 50, 100, 200, 500, 1000 ppm THPS. Then, each of these samples were mixed with and 1 mM $KMnO_4$ in MilliQ water (pH 5.0) in equal volumes and allowed to react for approximately 2 minutes. The intensity of the $KMnO_4$ absorption at 525 nm was then measured and normalized by subtracting the background intensity at 650 nm. This process was then repeated but using a pure THPS instead of a THPS-containing biocide. The series of samples containing pure THPS (at equal concentrations as shown above for the biocide product) were then compared to the biocide-containing samples.

Figure 4:
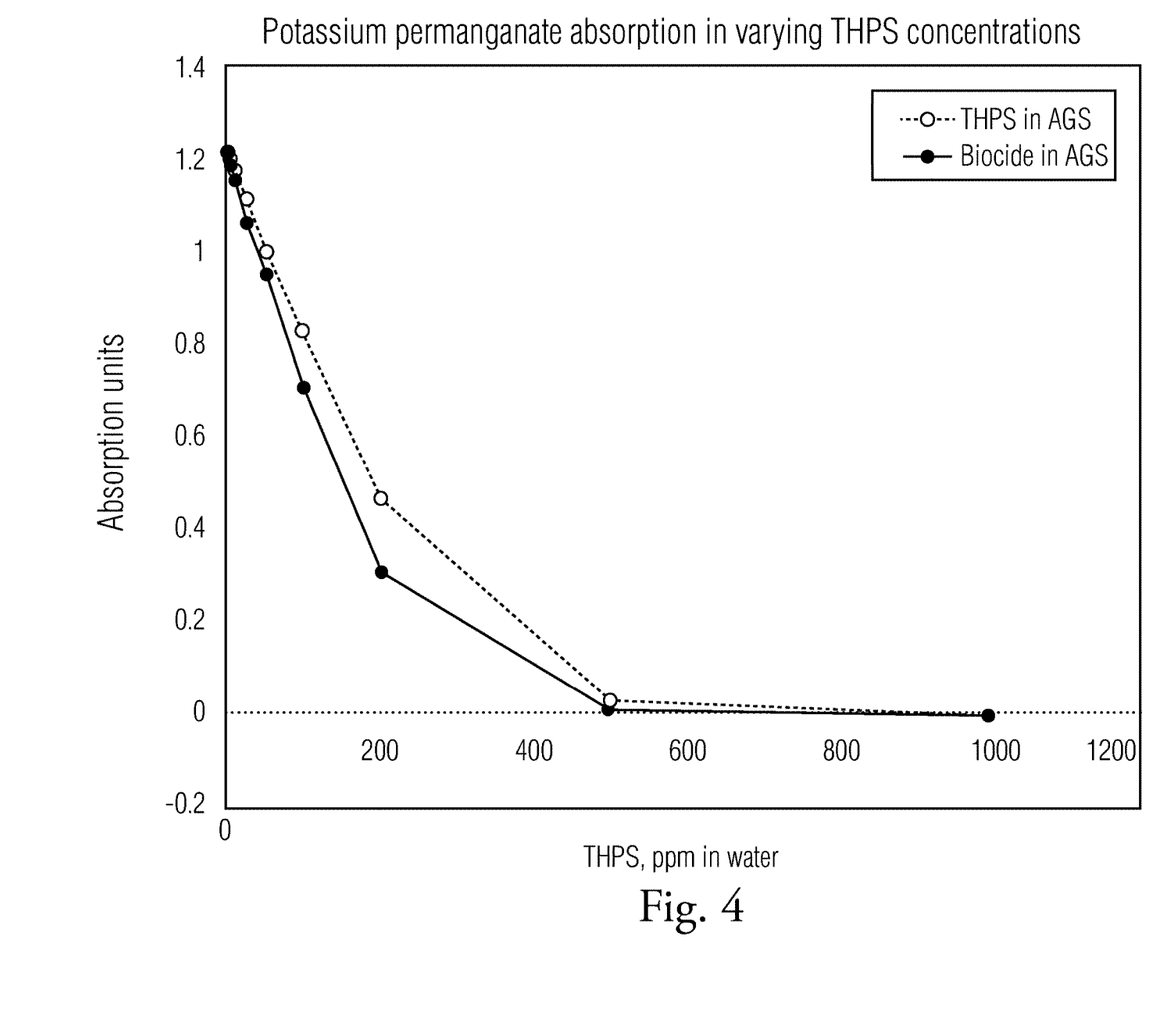
FIG. 4 displays a graph showing normalized measured $KMnO_4$ absorption as a function of approximate THPS concentrations (0-1000 ppm) in Arabian Gulf Seawater (AGS) samples containing a THPS-based biocide or pure THPS in accordance with one or more embodiments.
Figure 5:
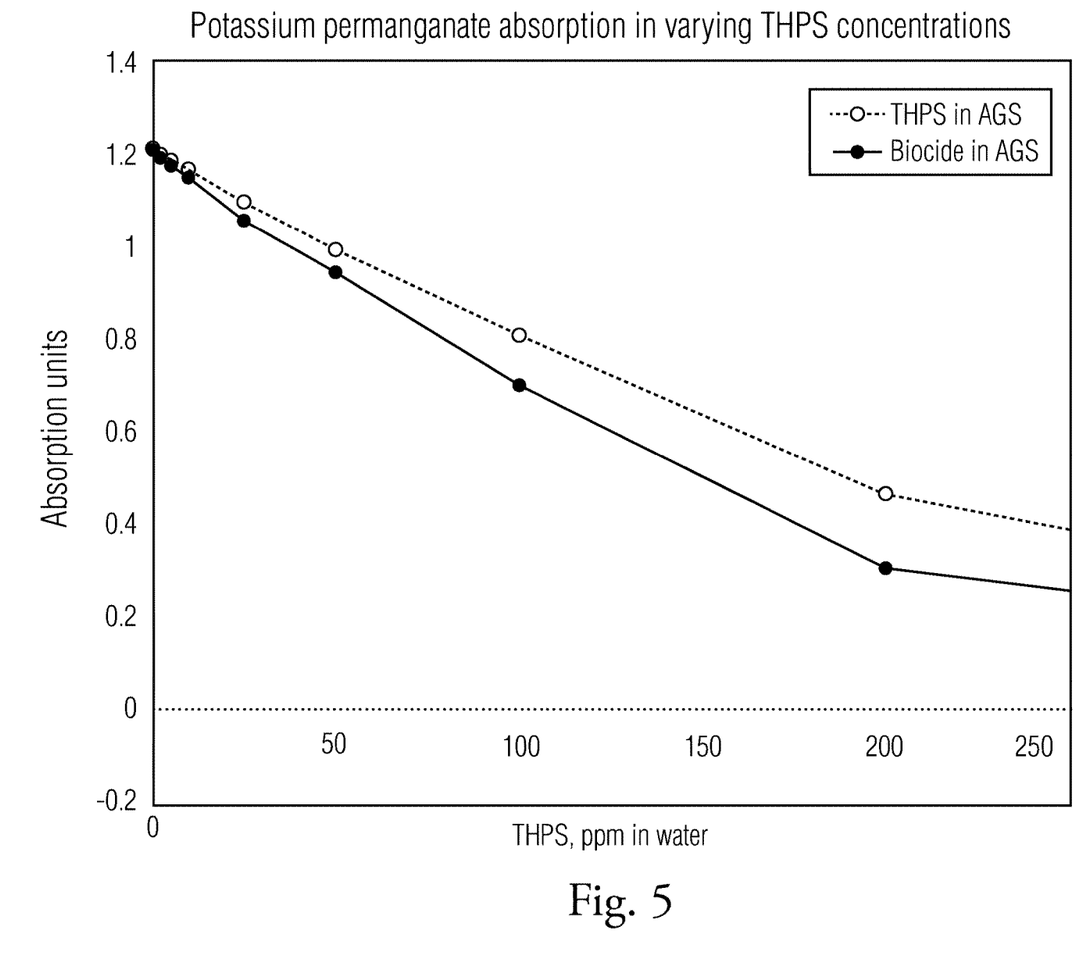
FIG. 5 displays a graph showing normalized measured $KMnO_4$ absorption as a function of approximate THPS concentrations (0-200 ppm) in AGS samples containing a THPS-based biocide or pure THPS in accordance with one or more embodiments.

FIG. 4 shows the normalized absorption as function of the approximate THPS concentrations in AGS for the THPS biocide-containing samples. For comparison, FIG. 4 also shows the corresponding samples containing pure THPS. FIG. 5 shows a zoomed in version of the graph of FIG. 4, focusing on the 0-200 ppm region of interest. As shown in FIGS. 4 and 5, $KMnO_4$ absorption is an effective way to measure the THPS content in AGS, with a linear range between 0 and 200 ppm, a dynamic range of approximately 2-500 ppm, and a limit of detection (LOD) of approximately 2 ppm. There is a small offset in the graphs of FIGS. 4 and 5 between the pure THPS and THPS-biocide product samples, both of which were diluted in AGS. The most plausible explanation is that the actual THPS content of the biocide product may be below the 30% approximation used in the preparation of THPS-biocide dilutions in the experiment.

Example 2

THPS samples of 0, 1, 4, 16, 64 and 256 ppm were prepared in fresh water, and 1.5 mL aliquots from each sample were transferred to respective reaction vials. Then 1.5 mL of acidic 0.6 mM $KMnO_4$ was added to each reaction vial, such that the THPS and the $KMnO_4$ reacted with one another. For each sample, 2 mL were transferred to an absorption cuvette and the absorption in the range of 400-700 nm was measured. This process was then repeated but using THPS samples in salt water (sea water) instead of fresh water.

Figure 6:
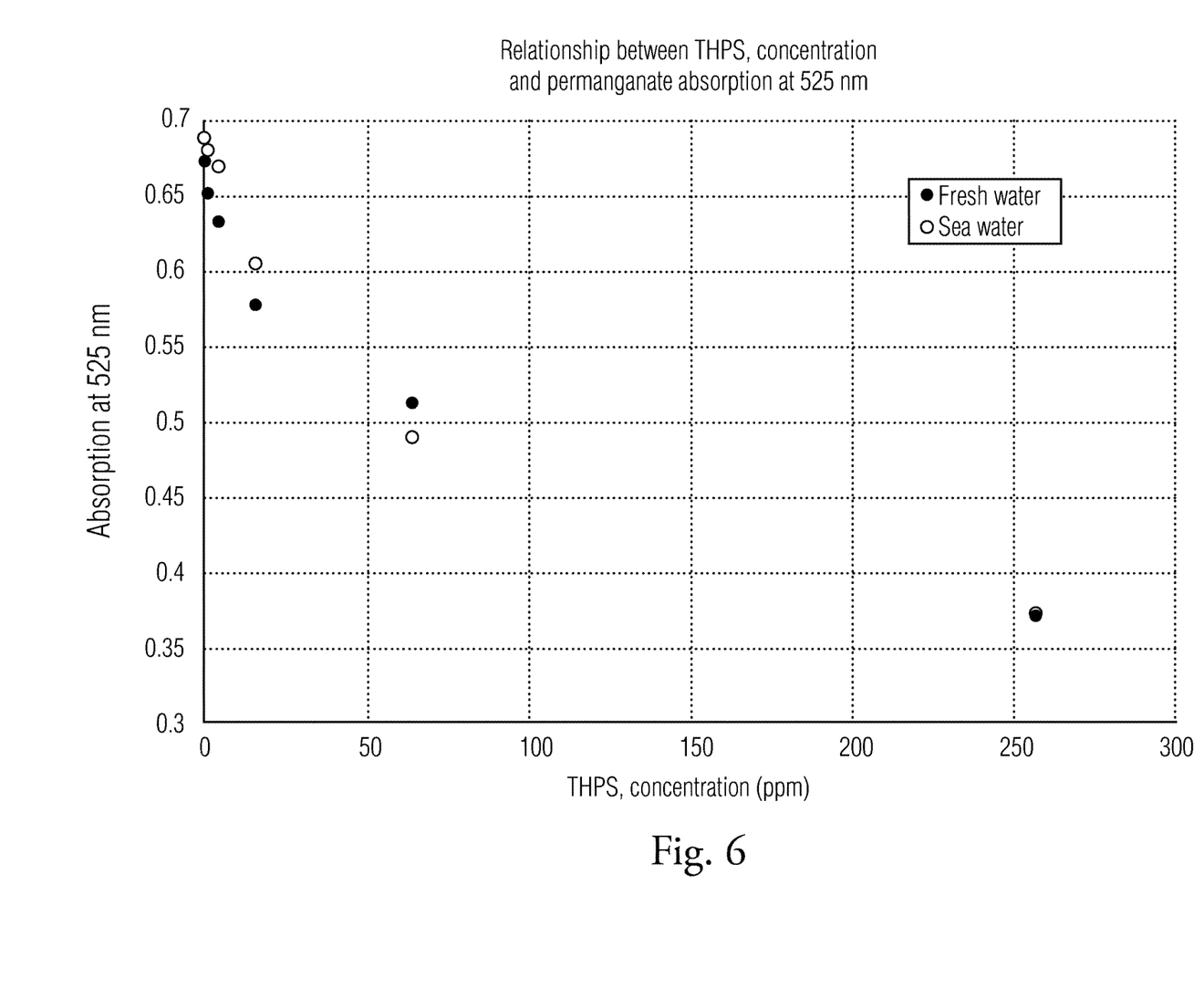
FIG. 6 shows an exemplary calibration curve showing the $KMnO_4$ absorption at 525 nm as a function of THPS concentrations in freshwater and saltwater samples in accordance with one or more embodiments.

FIG. 6 shows an exemplary calibration curve for freshwater and saltwater samples in accordance with one or more embodiments. As shown in the graph of FIG. 6, the $KMnO_4$ absorption decreases as the concentration THPS increases. Thus, a change in intensity of $KMnO_4$ absorption in the mixture is correlated with the concentration of THPS in the water sample. As such, based on this correlation, the calibration curve is established between the THPS concentration in given samples and the intensity of the $KMnO_4$ absorption.

Although much of the foregoing description has been directed to methods for methods detecting and quantifying THPS in a water sample, the methods disclosed herein can be similarly deployed and/or implemented in scenarios, situations, and settings far beyond the referenced scenarios. It should be further understood that any such implementation and/or deployment is within the scope of the methods described herein.

It is to be further understood that like numerals in the drawings represent like elements through the several figures, and that not all components and/or steps described and illustrated with reference to the figures are required for all embodiments or arrangements. Further, the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms " "including," "comprising," or "having," "containing," "involving," and variations thereof herein, when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Notably, the figures and examples above are not meant to limit the scope of the present disclosure to a single implementation, as other implementations are possible by way of interchange of some or all the described or illustrated elements. Moreover, where certain elements of the present disclosure can be partially or fully implemented using known components, only those portions of such known components that are necessary for an understanding of the present disclosure are described, and detailed descriptions of other portions of such known components are omitted so as not to obscure the disclosure. In the present specification, an implementation showing a singular component should not necessarily be limited to other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present disclosure encompasses present and future known equivalents to the known components referred to herein by way of illustration.

The foregoing description of the specific implementations will so fully reveal the general nature of the disclosure that others can, by applying knowledge within the skill of the relevant art(s), readily modify and/or adapt for various applications such specific implementations, without undue experimentation, without departing from the general concept of the present disclosure. Such adaptations and modifications are therefore intended to be within the meaning and range of equivalents of the disclosed implementations, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s). It is to be understood that dimensions discussed or shown are drawings are shown accordingly to one example and other dimensions can be used without departing from the disclosure.

The subject matter described above is provided by way of illustration only and should not be construed as limiting. Various modifications and changes can be made to the subject matter described herein without following the example embodiments and applications illustrated and described, and without departing from the true spirit and scope of the invention encompassed by the present disclosure, which is defined by the set of recitations in the following claims and by structures and functions or steps which are equivalent to these recitations.

What is claimed is:

1. A method for detecting tetrakis(hydroxymethyl)phosphonium sulfate (THPS) in a water sample, comprising:
    mixing a water sample with a $KMnO_4$ solution to form a mixture;
    measuring an intensity of $KMnO_4$ absorption in the mixture at a wavelength of 525 nm;
    normalizing the measured intensity by subtracting a background intensity at a wavelength of 650 nm; and
    determining a presence of THPS in the water sample by comparing the normalized intensity with intensity values of $KMnO_4$ absorption of calibration samples comprising $KMnO_4$ and known THPS concentrations.

2. The method of claim 1, wherein the water sample is mixed with the $KMnO_4$ solution for approximately 2 minutes.

3. The method of claim 1, wherein the water is fresh water or salt water.

4. The method of claim 3, wherein the salt water is Arabian Gulf Seawater.

5. The method of claim 1, wherein the mixture comprises equal volumes of the water sample and the $KMnO_4$ solution.

6. The method of claim 1, wherein the intensity of the $KMnO_4$ absorption in the mixture is measured using a sensor.

7. The method of claim 6, wherein the sensor comprises a 565 nm LED and a 650 nm LED attached to a Z-flow cell.

8. The method of claim 6, wherein the water sample is collected from water flowing in a conduit, and wherein the sensor is an online sensor in fluid connection with water conduit and configured to perform real-time measurements of the water flowing in the conduit.

9. The method of claim 1, wherein a limit of detection for THPS in the water sample is approximately 2 ppm.

10. A method for quantifying tetrakis(hydroxymethyl) phosphonium sulfate (THPS) in a water flowing in a conduit, comprising:
    mixing a water sample comprising THPS from the conduit with a $KMnO_4$ solution, wherein the THPS in the water sample reacts with the $KMnO_4$ solution;
    measuring an intensity of the $KMnO_4$ absorption in the mixture at a wavelength of 525 nm;
    normalizing the measured intensity by subtracting a background intensity at a wavelength of 650 nm; and
    determining a concentration of THPS in the water sample based on a comparison between the normalized intensity and intensity values of $KMnO_4$ absorption of calibration samples comprising $KMnO_4$ and known THPS concentrations.

11. The method of claim 10, wherein the determined concentration of THPS is accurate for water samples having a THPS content of approximately 2-500 ppm.

12. The method of claim 10, wherein the water sample comprises a THPS-based biocide.

13. The method of claim 10, wherein the water sample is mixed with the $KMnO_4$ solution for at least 2 minutes.

14. The method of claim 10, wherein the water is fresh water or salt water.

15. The method of claim 14, wherein the salt water is Arabian Gulf Seawater (AGS).

16. The method of claim 15, wherein the dynamic range of concentration of THPS in AGS is approximately 5-1500 ppm.

17. The method of claim 10, wherein the mixture comprises equal volumes of the water sample and the $KMnO_4$ solution.

18. The method of claim 10, wherein the intensity of the $KMnO_4$ absorption in the mixture is measured using a sensor.

19. The method of claim 18, wherein the sensor comprises a 565 nm LED and a 650 nm LED attached to a Z-flow cell.

20. The method of claim 18, wherein the sensor is an online sensor in fluid connection with the conduit and configured to perform real-time measurements.

* * * * *